United States Patent [19]

Scanlon et al.

[11] Patent Number: 5,585,363
[45] Date of Patent: Dec. 17, 1996

[54] CIRCUMVENTION OF HUMAN TUMOR DRUG RESISTANCE

[75] Inventors: Kevin J. Scanlon, Pasadena; Lawrence C. Sowers, Duarte, both of Calif.

[73] Assignee: City of Hope, Duarte, Calif.

[21] Appl. No.: 396,068

[22] Filed: Feb. 28, 1995

Related U.S. Application Data

[63] Continuation of Ser. No. 741,435, filed as PCT/US90/07155, Dec. 7, 1990, abandoned, which is a continuation of Ser. No. 447,593, Dec. 8, 1989, abandoned, which is a continuation-in-part of Ser. No. 436,691, Nov. 15, 1989, abandoned, which is a continuation-in-part of Ser. No. 421,342, Oct. 13, 1989, Pat. No. 5,166,140, which is a continuation-in-part of Ser. No. 234,096, Aug. 19, 1988, abandoned, which is a continuation-in-part of Ser. No. 46,127, May 5, 1987, abandoned.

[51] Int. Cl.$^6$ ..................... A61K 31/70; A61K 31/395; A61K 9/127

[52] U.S. Cl. .................. 514/45; 514/46; 514/49; 514/50; 514/210; 424/450

[58] Field of Search ................. 514/50, 45, 46, 514/210, 49; 424/450

[56] References Cited

U.S. PATENT DOCUMENTS

| 5,049,389 | 9/1991 | Radhakrishnan | 424/450 |
|---|---|---|---|
| 5,166,140 | 10/1992 | Scanlon et al. | 514/45 |

OTHER PUBLICATIONS

J. A. Double et al Anti–Cancer Drugs Design. 1:133–139, 1986.

*Primary Examiner*—John W. Rollins
*Attorney, Agent, or Firm*—Rothwell, Figg, Ernst & Kurz

[57] ABSTRACT

A method involving the administration of nucleoside analogs to circumvent resistance attributable to the enhanced DNA repair capacity of cancer cells is described. The nucleoside analogs function as suicide substrates for DNA repair enzymes. A method of screening nucleoside analogs for utility as antitumor agents and a screening assay to individual recurrent tumors is described.

11 Claims, 2 Drawing Sheets

CIRCUMVENTION OF HUMAN TUMOR DRUG RESISTANCE

This application is a continuation of U.S. application Ser. No. 741,435, filed as PCT/US90/07155, Dec. 7, 1990, now abandoned, which is a continuation of U.S. application Ser. No. 447,593 filed 8 Dec. 1989, now abandoned, which in turn is a continuation-in-part of U.S. application Ser. No. 436,691, filed 15 Nov. 1989, now abandoned, which, in turn, is a continuation-in-part of U.S. application Ser. No. 421,342 filed 13 Oct. 1989, now U.S. Pat. No. 5,166,100, which is a continuation-in-part of U.S. application Ser. No. 234,096 filed 19 Aug. 1988, now abandoned, which is a continuation-in-part of U.S. application Ser. No. 046,127 filed 5 May 1987, now abandoned.

BACKGROUND OF THE INVENTION

The efficacy for cancer therapy of radiation and drugs, such as cisplatin, is often limited by the development of resistance. Biochemistry and tissue culture studies indicate that such resistance is a function of the capacity of cancer cells to repair damaged DNA. Parent application Ser. No. 234,096, in accord with various published papers, demonstrates enhanced expression of DNA repair enzymes by DNA resistant phenotypes of certain human carcinoma cell lines. See, e.g., Lai, G. M., et al., *Biochem. Pharmacol.* 37:4597–4600 (1988); Hospers, G. A. P., et al., *Cancer Res.* 48:6803–6807 (1988); Masuda, H., et al., *Cancer Res.* 48:5713–5716 (1988); Kraker, A., et al., *Cancer Lett.* 38:307–314 (1988); Scanlon, K. J., et al., *Cancer Investigation* 7:563–589 (1989) (in press-incorporated herein by reference); and Scanlon, K. J., et al., *Anticancer Res.* 9:1301–1312 (1989) (incorporated herein by reference). See also, Murray, D., et al., *Cancer Res.* 45:6446–6452 (1985) and Miller, M. R., et al., *J. Biol. Chem.* 257:10204–10209 (1982).

AZT and various other nucleoside analogs are selective inhibitors of retroviral reverse transcriptases and of human DNA polymerases $\alpha$, $\beta$ and $\gamma$. See White, E. L., *Biochem. and Biophys. Res. Comm.* 161:393–398 (1989); Swinnen, L. J., et al., *Cancer Res.* 49:1383–1389 (1989); Ahnstrom, G., *Biochimica et Biophysica Acta* 1007:357–358 (1989); Elion, G. B., *Science* 244:41–47 (1989); Lin, T. -S., et al., *J. Med. Chem.* 32:1891–1895 (1989); Liu, S. -Y., et al., *Cancer Res.* 49:1366–1370 (1989); Oho, K., et al., *Mol. Pharmacol.* 35:578–583 (1989); Yarchoan, R., et al., *New Eng. J. Med.* 321:726–738 (1989) and U.S. Pat. No. 4,861,759.

SUMMARY OF THE INVENTION

This invention relates to the circumvention or amelioration of resistance attributable to an enhanced DNA repair capacity of cancer cells damaged by radiation or chemotherapy.

The parent application Ser. No. 234,096 states: "Properties that render human cancer cells resistant to chemotherapeutic drugs include enhanced expression of DNA repair enzymes and that new properties appear to enhance the sensitivity of the same cells to other drugs. For example, human leukemia cells resistant to cisplatin evidence enhanced sensitivity to dideoxy cytidine. Similarly, human ovarian cancer cells resistant to cisplatin have been shown to demonstrate increased sensitivity to AZT" (page 20, lines 8–14).

This phenomenon is observed because dideoxy cytidine (ddC), AZT and other nucleoside analogs are metabolized by cellular enzymes (kinases) to the triphosphates which serve as suicide substrates for DNA repair and replication enzymes, including among others DNA polymerase $\beta$. The consequent inhibition of DNA repair and replication enhances the cytotoxicity of radiation, DNA damaging chemotherapeutic agents and methotrexate in the resistant but not necessarily in the parental cell line.

The invention includes the discovery that the administration of certain nucleoside analogs, either alone or in combination with a DNA damaging agent such as radiation, cisplatin or methotrexate, avoids, ameliorates or circumvents human tumor cell resistance to such agents. Utilization of this discovery in the treatment of human patients is an important aspect of this invention.

When used in combination, sequential administration of the DNA damaging agent followed by administration of the nucleoside analog yields the desired result. The DNA damaging agent may also be administered simultaneously with the nucleoside analog, for example, by concurrent intravenous injection or by the use of liposomes in which the DNA damaging agent and nucleoside analog are co-entrapped.

Another aspect of the invention includes a method for screening nucleoside analogs and derivatives thereof for utility as antitumor agents.

The invention also provides a screening assay to individual recurrent tumors, whereby the susceptibility of such individual tumors to a panel of candidate nucleotide analogs is determined. Detection of increased activity of DNA repair enzymes by the polymerase chain reaction (PCR) assay described in Ser. No. 234,096 allows for the design of specific nucleoside analogs.

DETAILED DESCRIPTION OF THE INVENTION

Figure 1:
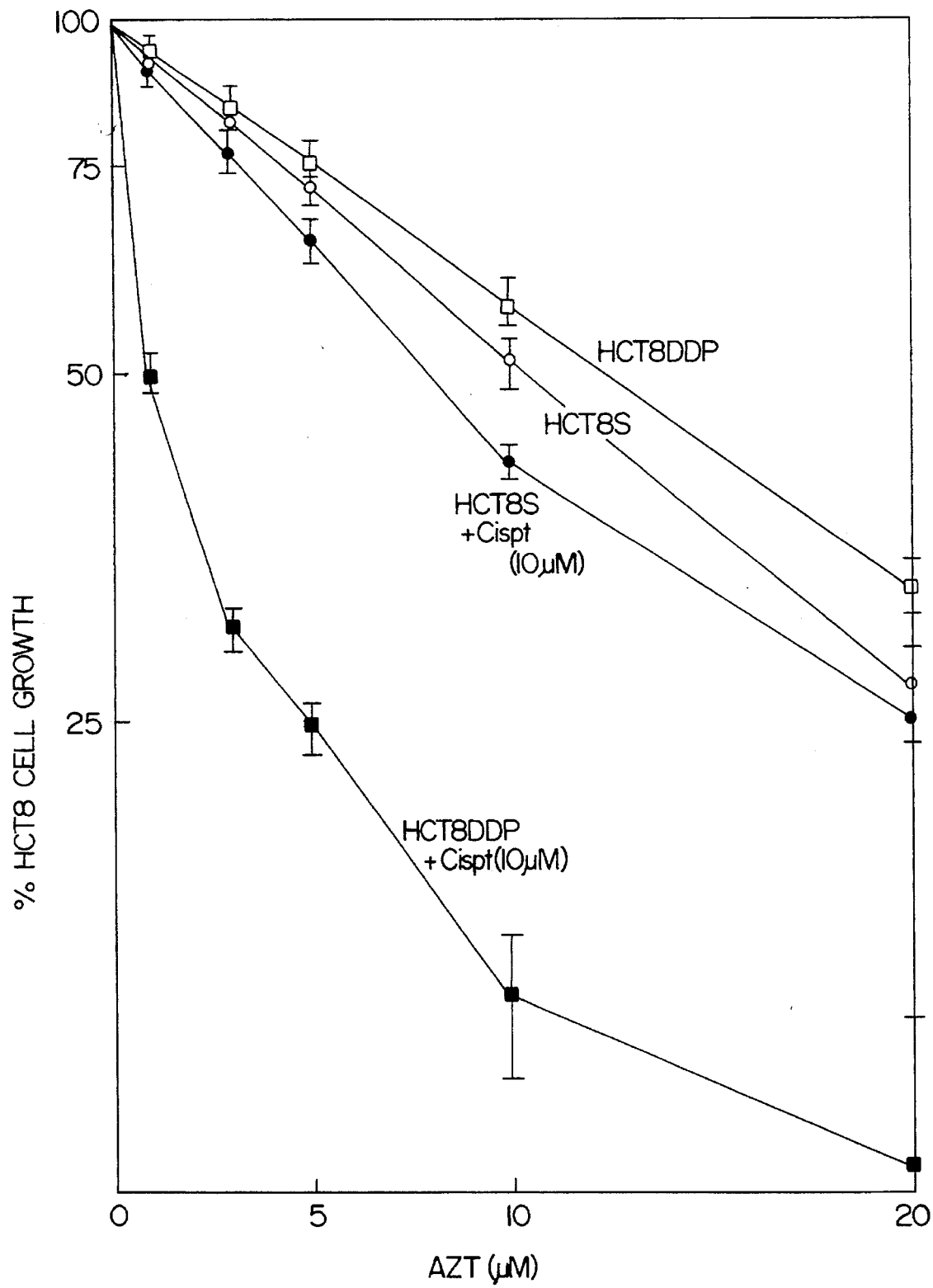

Some of the nucleoside analogs useful in this invention include those represented by Formula I and Formula II:

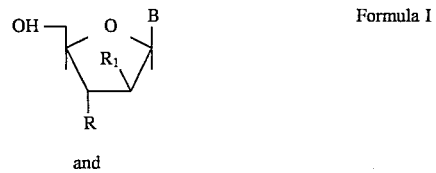

Formula I and

Formula II in which B is adenine, thymine, cytosine, guanine, inosine or a heterocyclic compound derived therefrom such as 5-methylcytosine and one or both of R and $R^1$ are halogen, preferably fluorine or iodine, azide, amine, hydrogen or hydroxyl.

An important part of the invention entails a recognition of the interdependence of three factors to achieve amelioration or circumvention of resistance, namely (i) whether the cells are sensitive or resistant, and if resistant, the degree of resistance, (ii) the type of cancer cell involved and (iii) the sequence in which the DNA damaging agent and nucleoside analog are administered. By an appropriate regimen implementing the consequences of such interdependence, resistance to DNA damaging therapy may be effectively treated.

For example, in instances where a specific nucleoside analog may be ineffective with a specific type of cancer resistant cells, pretreatment of such cells with, e.g., cisplatin may result in an effective regimen.

Specific nucleoside analogs useful in the invention include, but are not limited to, 3' azido-2',3' dideoxythymidine (AZT), dideoxy inosine (DDI), each of the purine nucleosides described in U.S. Pat. No. 4,861,759, and Yarchoan, supra, and ganciclovir which, as the triphosphate, is a potent inhibitor of DNA polymerase $\alpha$.

Table I illustrates the efficacy of ganciclovir as a suicide substrate evidenced by its toxicity to cisplatin resistant and sensitive A2780 cell lines.

TABLE I

Cytotoxic Studies with Ganciclovir in Human Carcinoma Cells Sensitive ("S") and Resistant (DDP) to Cisplatin

| Cell Line | $\alpha$DNA Polymerase Activity* | Ganciclovir $EC_{50}$ ($\mu$M) |
|---|---|---|
| A2780S | 95 (±6.7) | 110 (±2.1) |
| A2780DDP | 214 (±8.1) | 30 (±1.5) |
| HCT8S | 30.9 (±4.1) | 60 (±2.3) |
| HCT8DDP | 41.7 (±4.4) | 40 (±4.2) |

*The determination of DNA polymerase $\alpha$ was calculated as pmoles/$10^6$ cells/10 min (mean ± SD). The A2780 and HCT8 cells were plated in 35 mm petri dishes with RPMI 1640 nutrient. Twenty-four hours later, the cells were treated with 6 concentrations of ganciclovir in saline. The concentrations were in equal increments from 1 micromolar to 100 micromolar. Six days later the cells were counted on a Coulter Counter. The experiment was done in triplicate.

As indicated in Table I, A2780 cells resistant to cisplatin are 3–4 fold more sensitive to ganciclovir. This correlates with an approximate 2 fold increase in DNA polymerase $\alpha$ levels. A similar but more modest effect is observed for HCT8 cell lines for both DNA polymerase $\alpha$ levels and changes in ganciclovir sensitivity.

Table II reflects inhibition of A2780 cell sensitive (S) and resistant (DDP) growth by Cisplatin AZT Ara A, Ara C, and ddC. The experiment was conducted in triplicate in the manner described with respect to Table I.

TABLE II

Inhibition of A2780 cell growth by cancer chemotherapeutic agents $EC_{50}$ ($\mu$M)$^c$

| Compound | Treatment Time (hr) | A2780S | A2780DDP | Ratio$^a$ |
|---|---|---|---|---|
| Cisplatin | (1) | 7.0 (±1.4)$^b$ | 90.0 (±2.2)$^b$ | ±12.8 |
| AZT | C. exp.* | 10.0 (±1.1)$^b$ | 510.2 (±11.1)$^b$ | ±51.0 |
| araA | C. exp.* | 16.2 (±2.4)$^b$ | 64.7 (±6.1)$^b$ | ±4.0 |
| araC | C. exp.* | 0.1 (±0.01)$^b$ | 4.5 (±0.5)$^b$ | ±45.0 |
| ddC | C. exp.* | 1.5 (±0.8)$^b$ | 4.0 (±1.6)$^b$ | ±2.6 |

$^a$ratio of $EC_{50}$ of sensitive cells to that cells which denotes the degree of resistance of cross-resistance.
$^b$Mean ± SD
$^c$$EC_{50}$ is the concentration of drug that reduces cell proliferation by ½ during 6 days subsequent to an exposure with a cancer chemotherapeutic agent.
*C. exp. indicates continuous exposure.

The data in Table II indicates the degree of resistance is reduced by Ara A and ddC alone but increased by AZT and Ara C alone.

Table III illustrates the inhibition of A2780 cell growth by sequential treatment first with cisplatin and then with AZT, ddC and Ara A.

TABLE III

Inhibition of A2780 Cell Growth by Cancer Chemotherapeutic Agents.

| 1. Sequencing | $EC_{50}$ ($\mu$M)$^b$ A2780S | $EC_{50}$ ($\mu$M)$^b$ A2780DDP |
|---|---|---|
| (a) Cisplatin (1 hr) washout, AZT | 7.0 (+1.1)$^a$ | 10.0 (+1.1)ab) |
| (b) Cisplatin (1 hr), washout, ganciclovir | 64.0 | 30.0 |
| (c) Cisplatin (1 hr), washout, ddC | 0.2 (+0.02)$^a$ | 3.0 (+0.1)$^a$ |
| (d) Cisplatin (1 hr), washout, araA | 8.5 | 30.0 |

$^a$Mean + SD
$^b$$EC_{50}$ is the concentration of drug that reduces cell proliferation by ½ during 6 days subsequent to an exposure with a cancer chemotherapeutic agent.

A2780 cells were well-plated (35 mm dishes) and 24 hours later the cells were treated with cisplatin for 1 hr., washed out and then treated with 6 concentrations of from 1 $\mu$M to 100 $\mu$M increased in equal increments of a nucleoside analog in saline. Cells were then washed and incubated for 6 days. The cells were counted on a Coulter Counter and the experiment was done in triplicate.

As Table III also indicates, synergistic combinations are provided by administration of the nucleoside analogs of the invention sequentially with cisplatin or radiation. The combination of cisplatin and AZT is representative. AZT is a thymidine derivative metabolized via the thymidine metabolic pathway. The triphosphate AZTTP acts as a suicide substrate by causing DNA chain termination. See, White, E. L., *Biochem. and Biophys. Res. Comm.* 161:393–398 (1989).

Cisplatin cells are collaterally resistant to AZT alone and to the TTP antimetabolites. Increased TTP levels in cisplatin resistant cells results in a competitive disadvantage for AZTTP incorporation. To remove DNA adducts, resistant phenotype cells such as HCT8 cells resistant to cisplatin apparently metabolize their DNA more rapidly than sensitive cells. Repair gaps following cisplatin adduct removal provide sites for the incorporation of suicide substrates such as AZTTP. Sequential treatment of cancer cells, first with cisplatin and then AZT, enhances the reduction in cell growth. The exposure first to cisplatin enhances the capacity of the cells to synthesize and repair DNA damage which is then exploited by the administration of the suicide substrate AZTTP. This phenomenon is illustrated by FIG. 1.

To determine the biochemical basis for this selective synergy between cisplatin and AZT, the capacity of A2780DDP cells to repair DNA was quantitated. A dual labeled ($^{14}$C/$^3$H) experiment was designed to measure simultaneously DNA synthesis and degradation in response to cisplatin. In Table IV, A2780 cells were incubated for 48 hrs with ($^{14}$C) thymidine to label DNA, the A2780 cells were then exposed for 1 hr with ($^3$H) AZT prior to cisplatin (20 $\mu$M) addition. A2780S cells respond to cisplatin with a modest degradation (10%) of ($^{14}$C) DNA over 3 hrs. In contrast, A2780DDP degradation 40.5% of the ($^{14}$C) DNA in 3 hrs. A2780S responded to cisplatin with an increased (18.8%) incorporation of ($^3$H) AZT into trichloroacetic acid (TCA) soluble material; in contrast, A2780DDP cells incorporate 40.8% ($^3$H) AZT into TCA insoluble material over 3 hrs. Transplatin at equimolar concentrations (20 $\mu$M) had no influence on DNA synthesis or degradation in A2780 cells.

TABLE IV

Synthesis and Degradation of DNA in A2780 Cells Treated with Cisplatin

| Treatment Time (min) | $^{14}$C-Tdr/DNA | | 3H-AZT/DNA | |
|---|---|---|---|---|
| | A2780S | A2780DDP | A2780S | A2780DDP |
| 0 | 6.49 | 17.78 | 7.79 | 26.96 |
| 45 | 6.21 | 14.44 | 6.27 | 31.62 |
| 90 | 5.71 | 12.59 | 7.23 | 32.31 |
| 180 | 6.06 | 10.57 | 9.25 | 37.96 |

As Table V shows, this phenomenon in A2780DDP cells was not unique to AZT, both ddC and ara A were also incorporated into TCA precipitable material when treated with cisplatin (20 μM).

thymidine in DNA was stable in A2780 cells in the absence of cisplatin treatment. Only by the exposure to cisplatin was the DNA turnover increased significantly in A2780DDP cells. After 3 hrs, there were changes in the rate of DNA synthesis and repair in A2780DDP cells only as measured by $^{14}$C and $^3$H. This may be explained by changes in deoxynucleotide pools and/or selective repair of ($^3$H) AZT-DNA.

Any of the nucleoside analogs of this invention can be used in this sequential treatment protocol.

Table VI includes EC$_{50}$ data further exemplifying the invention. The data reported by Table VI was obtained by substantially the same procedure as that described with respect to Table III. In Table VI, "(C)" indicates continuous exposure, "(1 h)" and "(2 h)" indicate exposure for 1 hour and 2 hours; "HU" indicates hydroxyurea.

| Cell Lines | (C) ddA | (C) ddC | (C) ddG | (C) ddT | Pt+ ddC (C) | Pt+ AZT (C) | (C) AZT | (2 h) araC | (1 h) Cis Pt | (C) Cord-icpin | (C) Ribov-irin | (C) Acycl-ovir | (C) Ganci-clovir | (C) MU | (1 h) DAUR |
|---|---|---|---|---|---|---|---|---|---|---|---|---|---|---|---|
| A2780S | 10 (2) | 1.5 (3) | 60 | 110 | 0.2 | 7 (3) | 10 (2) | 0.1 (2) | 7 | 70 | 27 (2) | >300 | 110 | 75 | 100 |
| A2780 DDP | 25 | 4 (3)[a] | 110 | >750 | 3 (3) | 10 (2) | 510 (4) | 4.5 (2) | 90 | 310 | 45 (2) | >300 | 30 | 60 | 100 |
| MCF-7S | 30 | 2.5 | 210 | >500 | — | 6 | 65 (2) | 2.5 | 15 | 130 | 100 (2) | >300 | 200 | 100* | 58 |
| MCF-7 DDP | 30 | >100 | 180 | >500 | — | 0.5 | 10 (2) | 5 | 35 | — | — | >300 | 50 | 200 | 85 |
| HCT8S | 33 | 2 | 35 | >150 | 0.4 | 6 | 5.5 (2) | 29 | 30 | 110 | 70 | >300 | 60 | 100 | 11 |
| HCT8-DDP | 36 | 23 | 45 | >500 | 1.5 | 1 | 11 (2) | 79 | 100 | 95 | 50 | >300 | 40 | 100 | 15 |
| K562S | 37.5 (2) | 25 | 160 | >400 | — | — | 125 (2) | 0.3 | 6 | 130 (2) | 62 (2) | >300 | 10[b] | 40 | 9 |
| K562-DDP | 28 (2) | 5 | 190 | >400 | — | — | 150 (2) | 0.3 | 15 | 160 (2) | 75 (2) | >300 | 295 (2) | 140* | — |
| K562-araC | 36 (2) | >300 | 150 (2) | >400 | — | — | 70 (2) | 8.0 | 25 | 67 (2) | 42 (2) | >300 | 20[c] | 40 | 10 |
| K562-VP16 | 35 | 100 | 170 | 200 | — | — | 200 | 8.0 | 15 | 150 | 55 | >300 | 250 | 40 | — |

*Slow growth
Referring to Table VI:
(a) Figures in parentheses, e.g., (2), indicate replications of experiments.
(b) In applications Ser. No. 421,342 filed 13 October 1989 and Ser. No. 436,691 filed 15 November 1989, this value is reported as "135 (2)"; later data indicates that "10" is the more accurate value.
(c) In applications Ser. No. 421,342 filed 13 October 1989 and Ser. No. 436,691 filed 15 November 1989, this value is reported as "150 (2)"; later data indicates that "20" is the more accurate value.

TABLE V

Incorporation of Labelled Nucleoside Analogs into Macromolecules in A2780DDP Cells Treated with Cisplatin

| Substrate | After Cisplatin Treatment (min) | | | |
|---|---|---|---|---|
| | 0 | 45' | 90' | 180' |
| ($^3$H)AZT | 26.96 | 31.62 | 32.31 | 37.96 |
| ($^3$H)araA | 19.01 | 24.21 | 27.91 | 32.70 |
| ($^3$H)ddC | 15.09 | 36.94 | 42.61 | 45.93 |

If the A2780DDP cells were not pretreated with cisplatin, then a low level of ($^3$H) nucleoside analog incorporation in TCA soluble material was detected over three hours and was similar to the value at zero time. Also, the turnover of ($^{14}$C)

The data in Table VI indicates, inter alia, the following:
1. A2780:
Ovarian carcinoma cells become resistant to cisPt, requiring >12 fold more cisPt.
CisPt resistant cells can be killed with 3.3 fold LOWER ganciclovir concentration (30 uM).
By using cisPt in combination with AZT, both cisPt resistant and sensitive cells can be killed with equal efficiency.
2. MCF7:
Human breast cancer cells resistant to cisPt (by a factor of 2.3) are 4 fold MORE sensitive to ganciclovir and 6.5 fold more sensitive to AZT.
3. HCT8:
Human colon cancer cells which have become 2.7 fold resistant to cisPt are 1.5 fold more sensitive to ganciclovir.
4. K562:

Human leukemia cells resistant to cisPt are more sensitive to ddC by a factor of 5.

Human leukemia cells resistant to araC are 2 fold more sensitive to cordecepin and AZT.

CEM cells were made 15.8-fold resistant to methotrexate (MTX) by weekly (2 hr) pulses and cloned in soft agar. The optimal growth requirements for the CEMS/S and CEM/MTX for folinic acid cells were 2 nM and 10 nM. If the cells were grown in higher concentrations of folinic acid ($10^{-7}$M), both cell lines were correspondingly more resistant to MTX. In contrast, fluoropyrimidine cytotoxicity was enhanced in both cell lines with increasing concentrations of folinic acid from $10^{-7}$M to $10^{-6}$M. At concentrations of folinic acid that are not optimal for cell growth, both CEM cell lines are hypersensitive to fluoropyrimidines. In addition, CEM/MTX cells are more hypersensitive to fluoropyrimidines than CEM/S cells at ($10^{-8}$M) folinic acid or lower concentrations.

Figure 2:
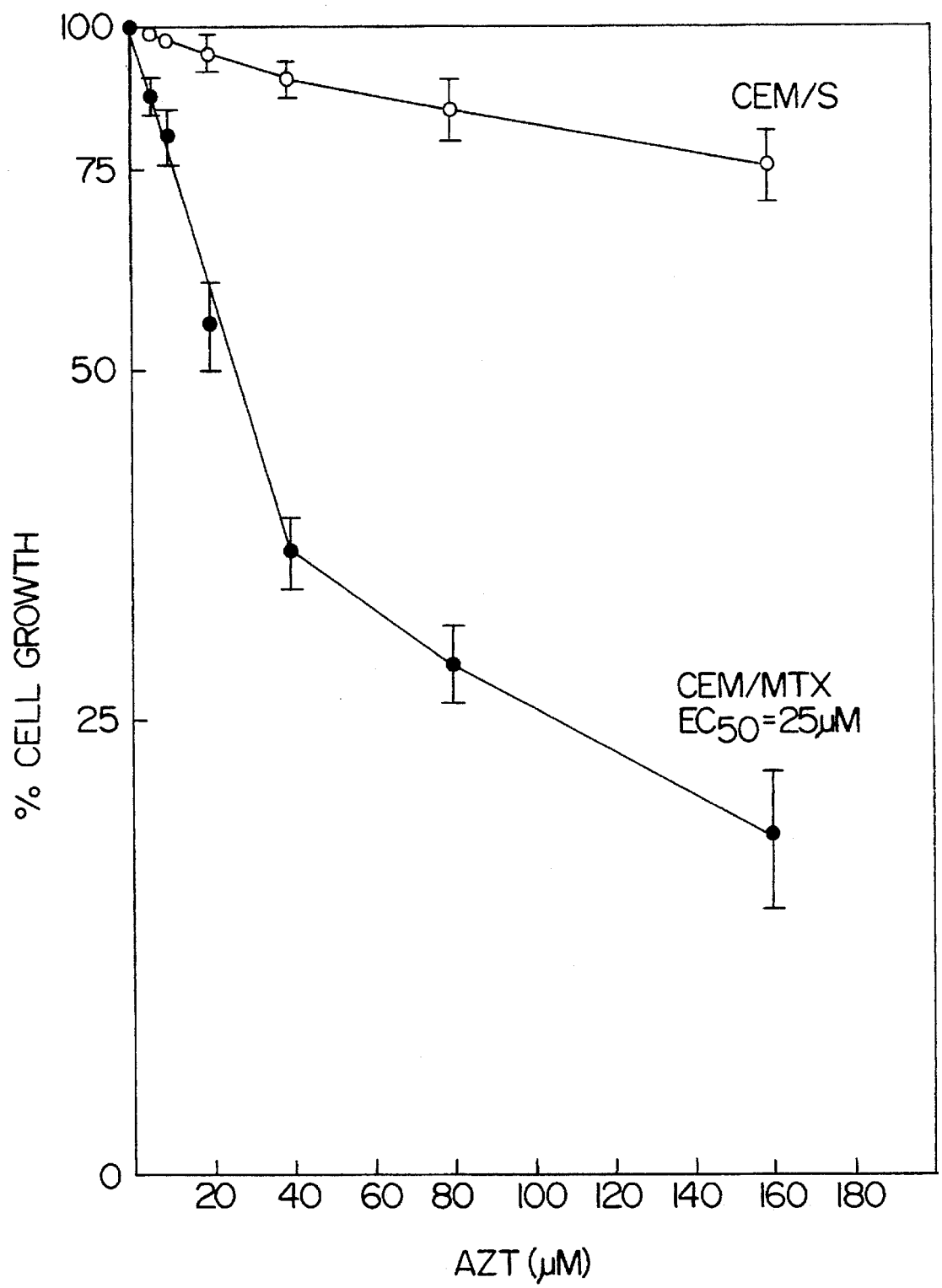

There was an increase in DHFR enzyme activity (11.07-fold) due to an eight-fold increase in DHFR gene amplification and expression in CEM/MTX cells. There was also a corresponding 2-fold increase in thymidine kinase (TK) enzyme activity and TK gene expression in CEM/MTX cells. AZT by continuous exposure (up to 160 μM) showed minimal cytotoxicity in CEM/S cells (FIG. 2). To obtain the data depicted by FIG. 2, CEM/S and CEM/MTX cells were continuously exposed to AZT (1–160 μM). CEM cells untreated with nucleoside analog were the controls (100%). The experiment was performed three separate times in duplicate. In contrast, CEM/MTX were collaterally sensitive to AZT ($EC_{50}$, 25 μM). dTMP synthase remained unchanged in both cell lines.

There was no change in dTMP synthase as measured by gene expression or enzyme activity, but the CEM/MTX cells were shown to have 2-fold elevation in TK activity. This may help CEM/MTX cells to salvage more thymidine, creating less dependence on dTMP synthase. Based on this unique property of CEM/MTX cells, preliminary evidence suggests that AZT can be activated via the thymidine metabolic pathway by the increased TK activity in CEM/MTX cells. Higher concentrations of AZTTP could be achieved in CEM/MTX cells, in contrast to CEMS cells, thus AZTTP would act as a more efficient suicide substrate by causing chain termination. Other deoxynucleoside analogs are currently under investigation to further exploit their selectivity against drug resistant cells. The DNA polymerase α and β are not increased in CEM/MTX cells, and this may explain the lack of cross resistance to AZT as seen in cisplatin resistant cells. It would be of interest clinically if MTX resistant cells could be exploited by the currently available nucleoside analogs. Patients that fail MTX treatment could easily be tested by the PCR assay for changes in gene expression of TK.

Table VII reflects data derived from the T-cell lymphocyte leukemia cell line "CEM":

TABLE VII

Nucleoside Analogs Effective Against Human Tumors

|    | Cell Line | Drug | $EC_{50}$ (μM)* |
|----|-----------|------|-----------------|
| 15.| CEMS      | AZT  | N.E.**          |
| 16.| CEMDDP    | AZT  | N.E.**          |
| 17.| CEMMTX    | AZT  | 25.0            |

\* = Continuous exposure.
\*\*N.E. = No effect with the nucleoside analogs.

The treatment of human patients is an important aspect of the invention. Serum levels of nucleoside analogs are achievable to micromolar range which is effective to kill resistant cells. Preferably, an appropriate nucleoside analog is administered intravenously in a therapeutically effective amount, e.g., about 10 mg/kg body weight, while suspended or dissolved in an appropriate carrier such as water.

Nucleoside analogs, either alone or in combination with a DNA damaging chemotherapeutic agent, may be encapsulated in liposomes for delivery to a tumor site in a patient's body. Such liposomal products may be produced in a known manner. See, generally, U.S. Pat. Nos. 4,797,285 and 4,873,088, each incorporated herein by reference.

This aspect of the invention, accordingly, includes nucleoside analogs of Formula I and Formula II encapsulated in liposomes. It also includes liposomes in which such nucleoside analogs are co-entrapped in the same liposome with a DNA damaging agent. Such agents include, but are not limited to, cisplatin and methotrexate. More specifically, the invention includes liposomes in which one or more of AZT, ganciclovir, AraA, AraC or ddC is co-entrapped with cisplatin or methotrexate. Although sequential administration of the DNA damaging agent and then of the nucleoside analog is preferred, particularly in human therapy, simultaneous administration is appropriate. It appears that such simultaneous administration results in the DNA damaging agent having the desired effect prior to the time that the nucleoside analog reaches peak effectiveness.

What is claimed is:

1. A method of preventing, circumventing or ameliorating resistance of human tumor cells to a DNA damaging chemotherapeutic agent, or to methotrexate or to radiation which comprises administering to a human patient a liposome encapsulated nucleoside analog of Formula I or Formula II in an amount therapeutically effective to inhibit the DNA repair function of said cells.

2. A method as defined by claim 1 in which said tumor cells are ovarian tumor cells.

3. A method as defined by claim 1 or claim 2 in which said nucleoside analog is AZT, ganciclovir, AraA, AraC or ddC.

4. A method as defined by claim 1 or claim 2 in which said nucleotides analog is co-entrapped in said liposome with a DNA Damaging chemotherapeutic agent.

5. A liposome having a DNA damaging agent and a nucleoside analog of Formula I or Formula II entrapped therein.

6. A method of treating a patient having cancer cells that are resistant to a DNA-damaging therapy, wherein such resistance is attributable to an enhanced DNA repair capacity of said cells, which method comprises, administering to said patient therapeutically effective amounts of said DNA-damaging therapy and a compound that is a suicide substrate for a DNA repair and replication enzyme or is converted in vivo to a suicide substrate for a DNA repair and replication enzyme.

7. The method of claim 6, wherein the DNA-damaging therapy is the administration of a DNA-damaging chemotherapeutic agent, methotrexate or radiation.

8. The method of claim 7, wherein the DNA-damaging therapy is the administration of a DNA-damaging chemotherapeutic agent.

9. The method of claim 7, wherein the DNA-damaging chemotherapeutic agent is cisplatin.

10. The method of claim 6, 7, 8 or 9, wherein said compound is a nucleoside analogue.

11. The method of claim 10, wherein said nucleoside analogue is ddA, ddC or ddI.

* * * * *